United States Patent
Engel et al.

(10) Patent No.: US 8,855,265 B2
(45) Date of Patent: Oct. 7, 2014

(54) CORRECTION METHOD FOR DIFFERENTIAL PHASE CONTRAST IMAGING

(75) Inventors: Klaus Juergen Engel, Aachen (DE); Dieter Geller, Aachen (DE); Gereon Vogtmeier, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 280 days.

(21) Appl. No.: 13/319,527

(22) PCT Filed: Jun. 10, 2010

(86) PCT No.: PCT/IB2010/052577
§ 371 (c)(1),
(2), (4) Date: Nov. 9, 2011

(87) PCT Pub. No.: WO2010/146503
PCT Pub. Date: Dec. 23, 2010

(65) Prior Publication Data
US 2012/0099702 A1    Apr. 26, 2012

(30) Foreign Application Priority Data

Jun. 16, 2009  (EP) .................... 09162764

(51) Int. Cl.
- *G03H 5/00* (2006.01)
- *A61B 6/00* (2006.01)
- *G21K 1/06* (2006.01)
- *G01N 23/04* (2006.01)

(52) U.S. Cl.
CPC . *A61B 6/00* (2013.01); *A61B 6/484* (2013.01); *G21K 2207/005* (2013.01); *G21K 1/06* (2013.01); *A61B 6/4092* (2013.01); *A61B 6/4291* (2013.01); *G01N 23/04* (2013.01)
USPC .............................. 378/62; 378/36

(58) Field of Classification Search
USPC ....................................... 378/62, 36
See application file for complete search history.

(56) References Cited

U.S. PATENT DOCUMENTS

| 6,150,973 A | 11/2000 | Pritt |
| 2011/0235775 A1* | 9/2011 | Tada ............................... 378/36 |

FOREIGN PATENT DOCUMENTS

| EP | 1731099 A1 | 12/2006 |
| EP | 1879020 A1 | 1/2008 |

OTHER PUBLICATIONS

Gianfranco Fornaro et al, "Global and local phase-unwrapping techniques: a comparison", Journal of the Optical Society, A, vol. 14, No. 10, Oct. 1, 1997, pp. 2702-2708. XP-002601257.

(Continued)

*Primary Examiner* — Hoon Song

(57) ABSTRACT

The present invention generally refers to a correction method for grating-based X-ray differential phase contrast imaging (DPCI) as well as to an apparatus which can advantageously be applied in X-ray radiography and tomography for hard X-ray DPCI of a sample object or an anatomical region of interest to be scanned. More precisely, the proposed invention provides a suitable approach that helps to enhance the image quality of an acquired X-ray image which is affected by phase wrapping, e.g. in the resulting Moiré interference pattern of an emitted X-ray beam in the detector plane of a Talbot-Lau type interferometer after diffracting said X-ray beam at a phase-shifting beam splitter grating. This problem, which is further aggravated by noise in the obtained DPCI images, occurs if the phase between two adjacent pixels in the detected X-ray image varies by more than $\pi$ radians and is effected by a line integration over the object's local phase gradient, which induces a phase offset error of $\pi$ radians that leads to prominent line artifacts parallel to the direction of said line integration.

20 Claims, 4 Drawing Sheets

(56) References Cited

OTHER PUBLICATIONS

Atsushi Momose et al, "Phase Tomography by X-ray Talbot Interferometry for Biological Imaging", Japanese Journal of Applied Physics, Japan Society of Applied Physics, vol. 45, No. 6A, Jun. 1, 2006, pp. 5254-5262, XP002444795.

Ming Jiang, Christopher Lee Wyatt, and GE Wang, "X-ray Phase-Contrast Imaging With Three 2D Gratings", International Journal of Biomedical Imaging, vol. 2008, 827152, Jun. 1, 2008, XP002601258.

Timm Weitkamp et al, "X-ray phase imaging with a grating interferometer", Optics Express, vol. 13, No. 16, pp. 6296-6304 Aug. 8, 2005.

A. Snigirev et al, "On the possibilities of x-ray phase contrast microimaging by coherent high-energy synchrotron radiation", Rev. Schi. Instrum 66 (12), Dec. 1995, pp. 5486-5492.

F. Pfeiffer, C. Kottler et al, "Hard X-Ray Phase Tomography with Low-Brilliance Sources", Physical Review Letters, 2007, vol. 98, Article ID. 108105-1-108105-4.

F. Pfeiffer, O. Bunk et al, "Shearing Interferometer for Quantifying the Coherence of Hard X-Ray Beams", Physical Review Letters, Apr. 29, 2005, Article 164801, 164801-1-164801-4.

Franz Pfeiffer et al, "Phase retrieval and differential phase-contrast imaging with low-brilliance X-ray sources", Nature Physics, vol. 2, Apr. 2006, pp. 258-261.

A. Olivo and R. Speller, "Modelling of a novel x-ray phase contrast imaging technique based on coded apertures", Phys. Med. Biol. 52, pp. 6555-6573, 2007.

K.A. Nugent et al, "Quantitative Phase Imaging Using Hard X Rays", Phys. Rev. Lett. 77, No. 14, Sep. 30, 1996, pp. 2961-2964.

A. Momose et al, "Phase-contrast x-ray computed tomography for observing biological specimens and organic materials", Rev. Sci. Instrum. 66 (2) Feb. 1995, pp. 1434-1436.

C. Kottler and C. David, "A two-directional approach for grating based differential phase contrast imaging using hard x-rays", Feb. 5, 2007, Optics Express, vol. 15, No. 3, 1175-1181.

M. Jiang et al, "X-Ray Phase-Contrast Imaging with Three 2D Gratings", International Journal of Biomedical Imaging, vol. 2008, Article ID 827152, pp. 1-8.

Christian David et al, "Wet-etched diffractive lenses for hard X-rays", J. Synchrotron Rad. (2001), pp. 1054-1055.

Peter Cloetens et al, "Hard x-ray phase imaging using simple propagation of a coherent synchrotron radiation beam", J. Phys., D. 32 (1999), pp. A145-A151.

P. Cloetens et al, "Observation of microstructure and damage in materials by phase sensitive radiography and tomography", J. Appl. Phys. 81 (9), May 1, 1997, pp. 5878-5886.

U. Bonse and M. Hart, "An X-ray Interferometer", Applied Physics Letters, vol. 6, No. 8, Apr. 15, 1965, pp. 155-157.

F. Beckmann et al, "Three-Dimensional Imaging of Nerve Tissue by X-Ray Phase-Contrast Microtomography", Biophysical Journal, Biophysical Journal, vol. 76, Jan. 1999, pp. 98-102.

M.R. Arnison et al, "Linear phase imaging using differential interference contrast microscopy", Journal of Microscopy, vol. 214, Apr. 1, 2004, pp. 7-12.

M. Ando and S. Hosoya, "An Attempt at X-ray Phase-Contrast Microscopy", Univ. of Tokyo Press, Tokyo, 1972, pp. 63-68.

* cited by examiner

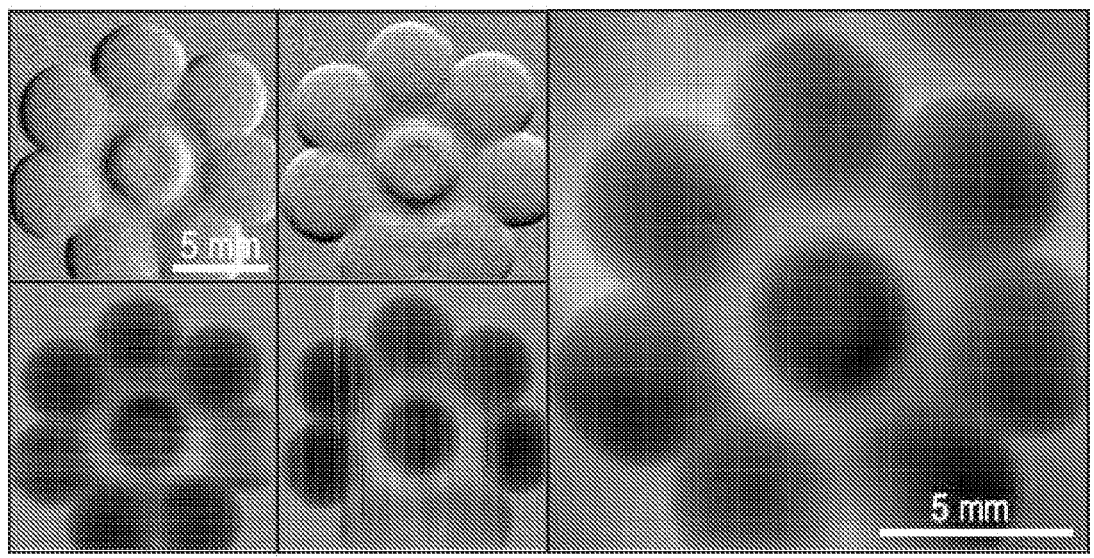
FIG. 4a  FIG. 4b  FIG. 4c
FIG. 4d  FIG. 4e
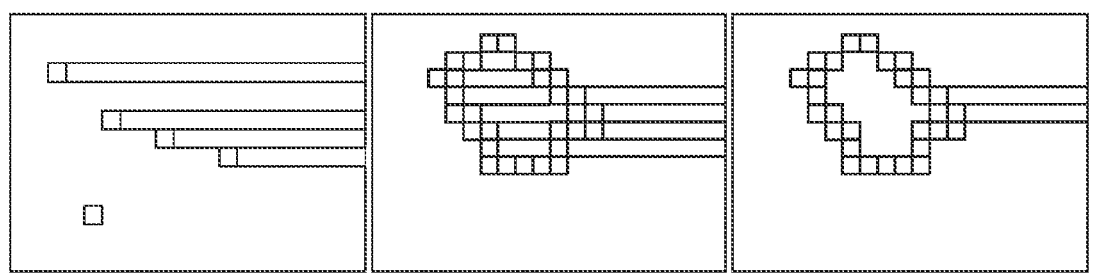
FIG. 5a  FIG. 5b  FIG. 5c

CORRECTION METHOD FOR DIFFERENTIAL PHASE CONTRAST IMAGING

FIELD OF THE INVENTION

The present invention generally refers to a correction method for grating-based X-ray differential phase contrast imaging (DPCI) as well as to an apparatus which can advantageously be applied in X-ray radiography and tomography for hard X-ray DPCI of a sample object or an anatomical region of interest to be scanned. More precisely, the proposed invention provides a suitable approach that helps to enhance the image quality of an acquired X-ray image which is affected by phase wrapping, e.g. in the resulting Moiré interference pattern of an emitted X-ray beam in the detector plane of a Talbot-Lau type interferometer after diffracting said X-ray beam at a phase-shifting beam splitter grating. This problem, which is further aggravated by noise in the obtained DPCI images, occurs if the phase between two adjacent pixels in the detected X-ray image varies by more than $\pi$ radians and is effected by a line integration over the object's local phase gradient, which induces a phase offset error of $2\pi$ radians that leads to prominent line artifacts parallel to the direction of said line integration.

BACKGROUND OF THE INVENTION

X-ray radiography and tomography are important methods for a variety of applications, such as e.g. non-destructive investigation of bulk samples, quality inspection of industrial products and non-invasive examination of anatomical structures and tissue regions of interest in the interior of a patient's body, which is because the penetration depth of hard X-ray beams is rather high, which allows for recording sharp projections of the attenuation coefficient. X-ray imaging thereby yields excellent results where highly absorbing anatomical structures such as bones are embedded in a tissue of relatively weakly absorbing material. However, in cases where different kinds of tissue with similar absorption cross-sections are under examination (such as e.g. in mammography or angiography), X-ray absorption contrast is relatively poor. Consequently, since X-ray radiographs or tomographic data sets with sufficient amplitude contrast are often difficult to obtain, differentiating pathological from non-pathological tissue in an absorption radiograph obtained with a current hospital-based X-ray system remains difficult for certain tissue compositions. In particular for medical applications such as mammography, high radiation doses are required to provide a sufficient contrast-to-noise ratio, which severely strains the health of both the patient and the clinical staff.

To overcome these limitations, phase imaging is a promising alternative for radiography of weakly absorbing materials. Several methods to generate radiographic contrast from the phase shift of X-rays passing through a phase object have been investigated. These methods can be classified into interferometric methods, techniques using an analyzer, and free-space propagation methods. All these methods differ vastly in the nature of the signal recorded, the experimental setup, and the requirements on the illuminating radiation. As phase-sensitive imaging techniques require X-rays of high spatial and/or temporal coherence, most of them are either implemented in combination with crystal or multilayer optics, at synchrotron facilities, or they use low-power micro-focus X-ray tubes. As described in "Phase retrieval and differential phase-contrast imaging with low-brilliance X-ray sources" (Nature Physics, vol. 2, num. 4, 2006, pp. 258-261, March 2006, ISSN: 1745-2473) by F. Pfeiffer, T. Weitkamp et al., the required spatial and temporal coherence lengths, $\xi_s$ and $\xi_t$, usually range in the order of about 1 µm. Propagation-based methods can overcome the stringent requirements on the temporal coherence, and—according to Pfeiffer and Weitkamp—have been demonstrated to work well with a broad energy spectrum leading to a temporal coherence length $\xi_t$ of about 1 nm. However, as shown by these authors, they still require a typical spatial coherence length of $\xi_s \geq 1$ µm, which is currently only available from micro-focus X-ray sources (with correspondingly low power) or synchrotrons. These constraints have, until now, hindered the final breakthrough of phase-sensitive X-ray imaging as a standard method for medical or industrial applications.

The cross section for elastic scattering of hard X-rays in matter, which causes a phase shift of the wave passing through the object of interest, is usually much greater than that for absorption. For example, 17.5-keV X-rays that pass through a 50-µm-thick sheet of biological tissue are attenuated by only a fraction of a percent, while the phase shift in radians is close to $\pi$. Recording the X-ray phase shift rather than only the absorption thus has the potential of a substantially increased contrast. A variety of X-ray techniques are employed to detect the phase contrast of a sample, i.e. to convert it into an amplitude contrast in the image plane. Some techniques use the Fresnel diffraction of coherent hard X-rays at the edges of a phase object to significantly improve the visibility of an object in microradiography (see e.g. Snigirev, I. et al., "On the possibilities of X-ray phase contrast micro-imaging by coherent high-energy synchrotron radiation", Rev. Sci. Instrum. 66 (1995), pp. 5486-5492). In first approximation, the obtained intensity distribution is proportional to the Laplacian of the refractive index distribution such as described in "Observation of microstructure and damage in materials by phase sensitive radiography and tomography" (J. Appl. Phys. 81 (1997), pp. 5878-5886) by P. Cloetens et al. and in certain cases a reconstruction of a phase object from a single micrograph is possible (see Nugent, K. A. et al., "Quantitative phase imaging using hard X-rays", Phys. Rev. Lett. 77 (1996), pp. 2961-2964). In "Hard X-ray phase imaging using simple propagation of a coherent synchrotron radiation beam" (J. Phys., D. 32 (1999), pp. A145-A151) by P. Cloetens, W. Ludwig et. al., it is described that quantitative information on arbitrary phase objects can be obtained by numerically evaluating series of images acquired with the detector placed at different distances from the sample.

The most sensitive method to measure the phase shifts introduced to a wave front is interferometry. A set-up for a Mach-Zehnder type interferometer operated in the hard X-ray range was introduced in the article "An X-ray interferometer" (Appl. Phys. Lett. 6 (1965), pp. 155-157) by U. Bonse and M. Hart about four decades ago. It consists of three partially transmitting Bragg crystals used as beam splitter and recombining elements. The incoming light is split into two separated branches one of which passes through the sample while the other serves as an unperturbed reference beam. The two beams interfering at the exit of the interferometer give an intensity distribution that represents the difference in optical path and thus—if perfectly aligned—of the phase shift caused by the object. Ando and Hosoya pioneered phase contrast imaging with such a device in the early seventies (see M. Ando and S. Hosoya, in: G. Shinoda, K. Kohra, T. Ichinokawa (Eds.), Proc. 6th Intern. Conf. On X-ray Optics and Microanalysis, "Observation of Antiferromagnetic Domains in Chromium by X-ray Topography", Univ. of Tokyo Press, Tokyo, 1972, pp. 63-68), and more recent setups have produced large numbers of excellent phase contrast images and computer tomograms, e.g. of biological specimens, such as e.g. described in "Phase-contrast X-ray computed tomography for observing biological specimens and organic materials" (Rev. Sci. Instrum. 66 (1995), pp. 1434-1436) by A. Momose et al. as well as in "Three-dimensional imaging of nerve tissue by X-ray phase-contrast microtomography" (Biophys. J. 76 (1999), pp. 98-102) by F. Beckmann et al. The main technical difficulty lies in the extreme demands on the mechanical stability of the optical components, as the relative positions of the optical components have to be stable within a fraction of a lattice constant, i.e. to sub-Ångström dimensions. Therefore, Bonse-Hart interferometers are very difficult to handle, especially when made big enough to investigate large samples.

A frequently used imaging method for enhancing the contrast of an X-ray radiograph or tomographic image is given by grating-based X-ray differential phase contrast imaging (DPCI), which allows for a simultaneous acquisition of the object absorption as well as a differential phase along a projection line. This technique requires no spatially or temporally coherent sources, is mechanically robust, can be scaled up to large fields of view and provides all the benefits of contrast-enhanced phase-sensitive imaging. Moreover, DPCI is fully compatible with conventional absorption radiography and applicable to X-ray medical imaging, industrial non-destructive testing and all kinds of imaging applications using other types of low-brilliance radiation (such as e.g. neutron radiation). DPCI thus provides valuable additional information usable for contrast enhancement, material composition or dose reduction.

Recently, a group at Paul-Scherrer Institute in Villigen (Switzerland) has shown a simple realization of a new DPCI setup for a Talbot-Lau type hard-X-ray imaging interferometer which can advantageously be applied for medical imaging. In "Phase retrieval and differential phase-contrast imaging with low-brilliance X-ray sources" (Nature Physics, vol. 2, No. 4, 2006, pp. 258-261, March 2006, ISSN: 1745-2473) by F. Pfeiffer, T. Weitkamp et al., a grating interferometer using a differential phase contrast setup is proposed which can be efficiently used to retrieve quantitative phase images with polychromatic X-ray sources of low brilliance. Similarly to equivalent approaches in the visible light or soft X-ray range, it can be shown that two gratings can be used for DPCI using polychromatic X-rays from brilliant synchrotron sources. In the article of Pfeiffer and Weitkamp, it is described how the use of a third grating allows for a successful adaptation of the method to X-ray sources of low brilliance. The proposed setup of these two authors consists of a source grating $G_0$ with period $p_0$, a phase-shifting grating $G_1$ with period $p_1$ (which is placed in downstream direction behind an object O to be imaged and acts as a beam splitter) and an absorber grating $G_2$ with period $p_2$ (see FIGS. 1a and 1b). Source grating $G_0$, which may typically be realized as an arrayed aperture mask with transmitting slits, placed close to the X-ray tube anode, creates an array of individually coherent, but mutually incoherent sources. It effectively allows for the use of relatively large (i.e., square millimeter sized) X-ray sources without compromising on the coherence requirements of the DPCI method. The ratio $\gamma_0$ of the width of each line source to the source grating period $p_0$ should be small enough to provide sufficient spatial coherence for the DPC image formation process. To be more precisely, for a distance d between gratings $G_1$ and $G_2$ which is given corresponding to the first Talbot distance of $d=p_1^2/8\lambda$ with $\lambda$ being the wavelength of the emitted X-ray beam, a spatial coherence length of $\xi_s=\lambda l/\gamma_0 p_0 \geq p_1$ is required, where l denotes the distance between gratings $G_0$ and $G_1$. With a typical value of a few micrometers for period $p_1$, the required spatial coherence length $\xi_s$ is of the order of about 1 μm, similar to the requirements of other known methods (see "Phase retrieval and differential phase-contrast imaging with low-brilliance X-ray sources" (Nature Physics, vol. 2, num. 4, 2006, pp. 258-261, March 2006, ISSN: 1745-2473) by F. Pfeiffer, T. Weitkamp et al.). It is important to note that even for a setup with only two gratings ($G_1$ and $G_2$) no spatial coherence in the direction parallel to the grating lines is required, in contrast to propagation-based methods. As source grating $G_0$ may contain a large number of individual apertures, each creating a sufficiently coherent virtual line source, standard X-ray generators with source sizes of more than a square millimeter can be used efficiently. To ensure that each line source produced by $G_0$ constructively contributes to the image-formation process, the geometry of the setup should satisfy the condition $p_0=p_2 \cdot l/d$ (see FIGS. 1c-e). It is important to note that the total source size w only determines the final imaging resolution, which is given by wd/l. The arrayed source thus decouples spatial resolution from spatial coherence, and allows the use of X-ray illumination with coherence lengths as small as $\xi_s=\lambda l/w\sim 10^{-8}$ m in both directions, if the corresponding spatial resolution wd/l can be tolerated in the experiment. Finally, on the assumption that a temporal coherence of $\xi_t \geq 10^{-9}$ m is sufficient, it can be deduced that the method of Pfeiffer and Weitkamp (ibid.) requires the smallest minimum coherence volume $\xi_s^2 \cdot \xi_t$ for phase-sensitive imaging if compared with existing techniques. Alternatively to a grating $G_0$, a structured source can be used, as described by J. Baumann et al. in EP 1 803 398 A1. Here, the apertures of $G_0$ are replaced by spatially restricted emission areas of an X-ray source, which is for example represented by a structured anode in an X-ray tube.

The formation process of the resulting DPC image, which is formed by means of phase grating $G_1$ and absorber grating $G_2$, is similar to known methods such as Schlieren imaging or diffraction-enhanced imaging. It essentially relies on the fact that a phase object placed in the X-ray beam path causes a slight deflection of the beam transmitted through the phase object O (see FIG. 1b). The fundamental idea of DPC imaging depends on locally detecting these angular deviations. As described in "Hard X-ray phase tomography with low-brilliance sources" (Physical Review Letters, 2007, vol. 98, Article ID 108105) by F. Pfeiffer, C. Kottler et al., the obtained deflection angle α at phase grating $G_1$, and thus the phases of the intensity oscillations at each pixel position P(x, y), is directly proportional to the local gradient of the object's phase shift and can be quantified by the equation $$\alpha(x, y) = \frac{\lambda}{2\pi} \cdot \frac{\partial \Phi(x, y)}{\partial x} = \int_{-\infty}^{+\infty} \frac{\partial \delta(x, y, z)}{\partial x} dz, \quad (1)$$

wherein x denotes a transverse direction perpendicular to the interferometer setup's optical axis OA (given by the axis z of the central X-ray beam CXB) and perpendicular to the grating lines of gratings $G_0$, $G_1$ and $G_2$ (given by the y-axis of the three-dimensional Cartesian coordinate system in FIG. 1a), $\Phi(x, y)$ represents the phase profile of the incident wave front as a function of the two transverse directions x and y, λ is the wavelength of the incident X-rays, and δ(x, y, z) is the decrement of the real part of the object's refractive index n (x, y, z) from unity, i.e. n (x, y, z)=1−δ(x, y, z)+jβ(x, y, z), with β(x, y, z) denoting the imaginary part of this refractive index and j:=√−1 being the imaginary unit.

For weakly absorbing objects, the detected intensity is a direct measure of the object's local phase gradient $\partial\Phi(x, y)/\partial x$. The total phase shift of the object can thus be retrieved by a simple one-dimensional integration along the x-axis. A higher precision of the measurement can be achieved by splitting a single exposure into a set of images taken for different positions of the grating $G_2$. This approach also allows the separation of the DPC signal from other contributions, such as a non-negligible absorption of the object or an already inhomogeneous wave front phase profile before the object. The proposed method of Pfeiffer and Weitkamp is fully compatible with conventional absorption radiography, because it simultaneously yields separate absorption and phase-contrast images such that information is available from both.

A slight deflection angle $\alpha$, which yields a slight angle of incidence on phase grating $G_1$, results in a local displacement $\Delta x = d \cdot \tan(\alpha) \approx d \cdot \alpha$ (for $\alpha$ [rad]$<<1$) of the interference fringes at the distance d downstream of $G_1$. A local phase gradient $\partial\Phi(x, y)/\partial x$ caused by the index of refraction of the phase object O can therefore be translated into a local displacement $\Delta x$ of the interference fringes. Since the direct determination of the exact position of these fringes requires detectors with spatial resolution in the sub-micrometer range, an absorber grating $G_2$, which is realized as a mask of equidistant bars of gold and transmitting slits (see description of FIG. 1e below), is used for determining the average displacement $\Delta x$ of the fringes within a detector pixel. Absorber grating period $p_2$ thereby equals the periodicity of the undistorted interference pattern.

If absorber grating $G_2$ is stepped perpendicularly to the grating bars (which means in x-direction such as depicted in FIG. 1a) and individual pictures are taken in each position, the measured signal of each pixel becomes an oscillating function of the absorber grating position $x_g$ in x-direction. The position of the maximum in this periodic signal is proportional to the average displacement $\Delta x$, and thus to the aforementioned local phase gradient $\partial\phi(x, y)/\partial x$. Therefore, determining the average displacement shift $\langle \Delta x \rangle$ for each pixel yields an image of the phase gradient. Furthermore, the average over one period of this intensity oscillation is proportional to the transmitted intensity through the object and thus provides the absorption radiograph. Taking advantage of this phase-stepping acquisition mode, both the absorption image and the local phase gradient image can be measured at the same time. For hard X-rays with $\lambda<0.1$ nm, deflection angle $\alpha$ is relatively small, typically of the order of a few microradians. In the known setup described above, determination of this deflection angle is achieved by the arrangement formed by phase grating $G_1$ and absorber grating $G_2$. Most simply, it can be thought of as a multi-collimator which translates angular deviations into changes of the locally transmitted intensity that can be detected with a standard imaging detector.

By the way, it has to be noted that the principle of the Talbot-Lau type interferometer is not restricted to line gratings. According to M. Jiang et al. (in: Int. J. Biomed. Imaging, Article ID 827152, Vol. 2008), two-dimensional structured gratings allow to determine a phase gradient $\partial\Phi(x, y)/\partial x$ not only in one direction (x), but also a phase gradient $\partial\Phi(x, y)/\partial y$ in a direction (y) perpendicular to the x-direction, which is acquired by an additional phase stepping along the y-direction.

Another grating-based method to determine phase gradients $\partial\Phi(x, y)/\partial x$ and/or $\partial\Phi(x, y)/\partial y$ is proposed as "coded aperture" technique by A. Olivo and R. Speller (in: Phys. Med. Biol. 52, pp. 6555-6573 (2007)). In this method, a structured X-ray absorbing mask, named as "coded aperture", is placed directly in front of an object to be examined. This mask provides small apertures, similar to the grating $G_0$ in the Talbot-Lau type interferometer, which produce in case of a distant X-ray illumination an array of nearly parallel X-ray beams with a cross-sectional area, which is defined by the shape of the apertures. Therefore, a second coded aperture grating is placed directly in front of the detector. The apertures of the second mask are chosen such that a defined part of each X-ray beam is blocked, such that for each beam a predefined intensity is transmitted through the second mask. The detection unit behind the second mask is adapted such that the transmitted intensity of each X-ray beam is averaged and attached to one image pixel, respectively. As an object is put between the first and the second mask, each of said X-ray beams is diffracted by the object's structure, which results in an angular deflection of the beam as compared to the direction the beam would take in the absence of the object. The deflection of each beam causes a deviating signal for each beam in the detection unit, because the illumination area on the second mask is laterally translated. As a result, the signal acquired for each beam (meaning for each pixel) is proportional to the deflection of each beam, which therefore is proportional to a phase gradient $\partial\Phi(x, y)/\partial x$ if the masks consists of parallel lines in y-direction. It is also possible to determine the phase gradients $\partial\Phi(x, y)/\partial x$ and $\partial\Phi(x, y)/\partial y$ independently if two-dimensional patterned coded apertures are used, and the direction of each beam deflection is determined by an additional stepping and sampling process, for example by translating the second mask into the x- and y-directions and therefore determining the x-component and the y-component of the phase gradient vector projected onto the detector plane.

SUMMARY OF THE INVENTION

One major drawback of DPCI is $2\pi$ phase-wrapping, which may occur if the phase between two adjacent pixels (given in radians) varies by more than $\pi$. In this case, an offset error of $2\pi$ is induced after integration of the differential phase along a line as described by C. Kottler et al. in Optics Express 15 (3), p. 1175 (2007). This problem is aggravated by noise in the DPCI images. As a result, prominent line artifacts parallel to the direction of phase differentiation/integration appear (see FIGS. 4d and 4e). To solve this problem, Kottler et al. propose to rotate the DPCI setup by 90° around the optical axis, take a second DPCI image and subsequently combine both images. However, this approach is problematic for medical imaging, which is because a rotation of the setup during the clinical procedure is mechanically challenging as regards mechanical tolerances and precision accuracy. Furthermore, it requires a double exposure of the patient with X-rays, which is not acceptable for dose reasons.

In view thereof, it is an object of the present application to detect and correct for such phase wrappings so as to enhance the contrast of an obtained X-ray image. To solve this object, the present application proposes to use the information of the absorption image to detect phase wrappings and to correct for them.

A first exemplary embodiment of the present application refers to an apparatus for imaging an object by means of electromagnetic waves or matter waves, wherein the object causes an altered phase information of the electromagnetic waves or matter waves according to a local refraction index. According to a preferred aspect of this first exemplary embodiment, these electromagnetic waves may be given by X-ray radiation. The proposed apparatus comprises a radiation source for emitting the electromagnetic waves or matter waves transmitting said object, a radiation detector for detecting these electromagnetic waves or matter waves and a processing means for gaining information representative of the object's local phase gradient in at least one transverse direction perpendicular to the interferometer setup's optical axis. According to the present invention, said processing means is adapted for determining the pixel positions of noisy pixels and/or determining at which pixel positions of a detected phase gradient image the local phase gradient exceeds a predefined threshold value and marking all these pixels as "bad", performing a line integration over the local phase gradient, thus yielding an integrated phase gradient image, analyzing the integrated phase gradient image for characteristic line artifacts occurring behind pixels of strong phase gradient which have been marked as "bad" and introducing a correction phase offset of $2\pi$ radians or an integer multiple thereof at the position of each "bad" pixel if analysis shows that a measured $2\pi$ phase offset error or an integer multiple thereof between immediately adjacent line artifacts which is induced by said line integration persists after passing a pixel that has been marked as "bad" so as to compensate this $2\pi$ phase offset error or an integer multiple thereof.

The proposed apparatus may for example comprise a DPCI-based grating interferometer setup of the Talbot-Lau type for differential phase contrast imaging with said interferometer including at least one source grating for achieving spatial beam coherence, realized as an arrayed aperture mask with periodically modulated transmission and placed in downstream direction immediately behind the radiation source, at least one diffractive grating with a periodic structure, which serves as a phase-shifting beam splitter generating self-images according to the Talbot effect, at least one analyzer grating placed behind the at least one diffractive grating and in front of the radiation detector, wherein said radiation detector comprises a wave absorber with a periodical structured attenuation strength adapted to a self-image of the diffractive grating, and a volume which is large enough to place the object to be imaged anywhere between the at least one source grating and the at least one analyzer grating.

The at least one source grating and the at least one analyzer grating may both be realized as a periodic structure comprising a number of stripes oriented in parallel to a first direction perpendicular to the optical axis for creating an interference pattern which basically obtains a periodical modulation along a second direction perpendicular to the first direction and perpendicular to the optical axis.

As an alternative thereto, the at least one source grating and the at least one analyzer grating may both be realized as a periodic structure given by a two-dimensional array or lattice structure exhibiting a periodicity in at least two directions perpendicular to the optical axis for creating an interference pattern which basically obtains a periodical modulation along at least two directions perpendicular to the optical axis.

The proposed apparatus may optionally comprise at least one actuator means for shifting at least one of the gratings in a direction perpendicular to the optical axis and parallel to at least one direction which contains a periodicity of the self-image of when carrying out a phase-stepping approach, and further comprising controlling means for controlling said actuator means in such a way that at least one of said gratings is shifted by predefined fractions of the periodicity of the diffractive grating's self-image in accordance with said phase-stepping approach.

According to a special aspect of the present invention, it may be provided that the at least one source grating is either replaced by a wave source with a spatially modulated intensity distribution corresponding to the apertures of the replaced at least one source grating or by an array of at least one point source, wherein "point" represents an emission area small enough to fulfill the requirements of spatial coherence.

The local phase gradient mentioned above may be measured by use of coded apertures, characterized by at least two structured wave absorbing masks arranged behind the radiation source, wherein a first mask of these at least two structured wave absorbing masks may provide a plurality of wave beams having cross-sectional areas perpendicular to the beam direction which do not overlap each other, said wave beams optionally transmitting the object to be imaged, and wherein a second mask of the at least two structured wave absorbing masks may partially cover each of the cross-sectional areas of said wave beams before being detected by the radiation detector, wherein the cross-sectional area of each wave beam covered by said second mask and thus the signal detected by the radiation detector depends on the deflection of said wave beam proportional to the local phase gradient.

A second exemplary embodiment of the present application is directed to a method for reducing the influence of induced phase errors on the image quality of an interferometer setup for imaging an object by means of electromagnetic waves or matter waves, wherein the object causes an altered phase information of the electromagnetic waves or matter waves according to a local refraction index. As described above with reference to the first exemplary embodiment of the invention, said interferometer setup comprises a radiation source for emitting the emitting electromagnetic waves or matter waves transmitting said object, a radiation detector for detecting these electromagnetic waves or matter waves and a processing means for gaining information representative of the object's local phase gradient in at least one transverse direction perpendicular to the interferometer setup's optical axis. According to the present invention, said method comprises the steps of determining the pixel positions of noisy pixels and/or determining at which pixel positions of a detected phase gradient image the local phase gradient exceeds a predefined threshold value and marking all these pixels as "bad", performing a line integration over the local phase gradient, thus yielding an integrated phase gradient image, analyzing the integrated phase gradient image for characteristic line artifacts occurring behind pixels of strong phase gradient which have been marked as "bad" and introducing a correction phase offset of $2\pi$ radians or an integer multiple thereof at the position of each "bad" pixel if analysis shows that a measured $2\pi$ phase offset error or an integer multiple thereof between immediately adjacent line artifacts which is induced by said line integration persists after passing a pixel that has been marked as "bad" so as to compensate this $2\pi$ phase offset error or an integer multiple thereof. Preferably, it may be intended that this method is used for reducing the influence of induced phase errors on the image quality of a DPCI-based grating interferometer setup of the Talbot-Lau type for hard X-ray phase contrast imaging.

In case of detecting an image area within an interference pattern of the generated X-ray image which is completely surrounded by "bad" pixels, said method may thereby comprise the step of estimating the number of $2\pi$ phase offset errors between immediately adjacent line artifacts of the interference pattern before carrying out said determination step. Furthermore, it may be provided that said method comprises the step of estimating the number of $2\pi$ phase offset errors within this image area relative to the number of $2\pi$ phase offset errors outside this image area by calculating an averaged number of $2\pi$ phase offset errors both over the inside area and over the outside area and by applying a whole-area phase correction offset given by the sum over a number of $2\pi$ phase offsets which fits best to the difference of the two calculated average values.

As proposed by the present application, the claimed method is finished with the step of interpolating the phase offsets of "bad" pixels from that of "good" pixels in the neighborhood of said "bad" pixels. It may also be provided that information of an available absorption image is used for a better estimation of a correction offset for "bad" pixels.

A third exemplary embodiment of the present application is dedicated to the use of a method as described with reference to the second exemplary embodiment in the scope of a medical X-ray radiography, 3D rotational angiography or computed tomography application scenario for enhancing the image quality of acquired X-ray images.

Finally, a fourth exemplary embodiment of the present application refers to a computer program for carrying out a method as described with reference to said second exemplary embodiment when running on an integrated processing means of a workstation for controlling an apparatus as described with reference to the first exemplary embodiment.

BRIEF DESCRIPTION OF THE DRAWINGS

These and other advantageous aspects of the invention will be elucidated by way of example with respect to the embodiments described hereinafter and with respect to the accompanying drawings. Therein, FIG. 4c shows an absolute phase which results from the processing of the differential phase contrast images shown in FIGS. 4a+b, which exemplarily illustrates a removal of line artifacts that occur for a processing as described with reference to FIGS. 4d+e (ibid.), FIGS. 4d+e show the absolute phase contrast after individual line-wise integration of the differential phase contrast images shown in FIGS. 4a+b, wherein characteristic line artifacts along the direction of integration become visible (ibid.), FIG. 5a shows a first schematic diagram for graphically illustrating phase wrapping in the integrated phase gradient induced by random pixel noise, FIG. 5b shows a second schematic diagram for graphically illustrating wrapping of the integrated phase gradient inside and outside an image area which is surrounded by "bad" pixels having a strong phase gradient, and FIG. 5c shows a third schematic diagram for graphically illustrating the correction of the integrated phase gradient of the inside image area of FIG. 5b after having corrected the phase wrapping by means of the claimed method as proposed in the present application.

DETAILED DESCRIPTION OF THE EMBODIMENTS

In the following sections, an exemplary embodiment of the claimed DPCI setup according to the present invention will be explained in more detail referring to the accompanying drawings and starting with a brief description of the relevant prior art.

Figure 1A:
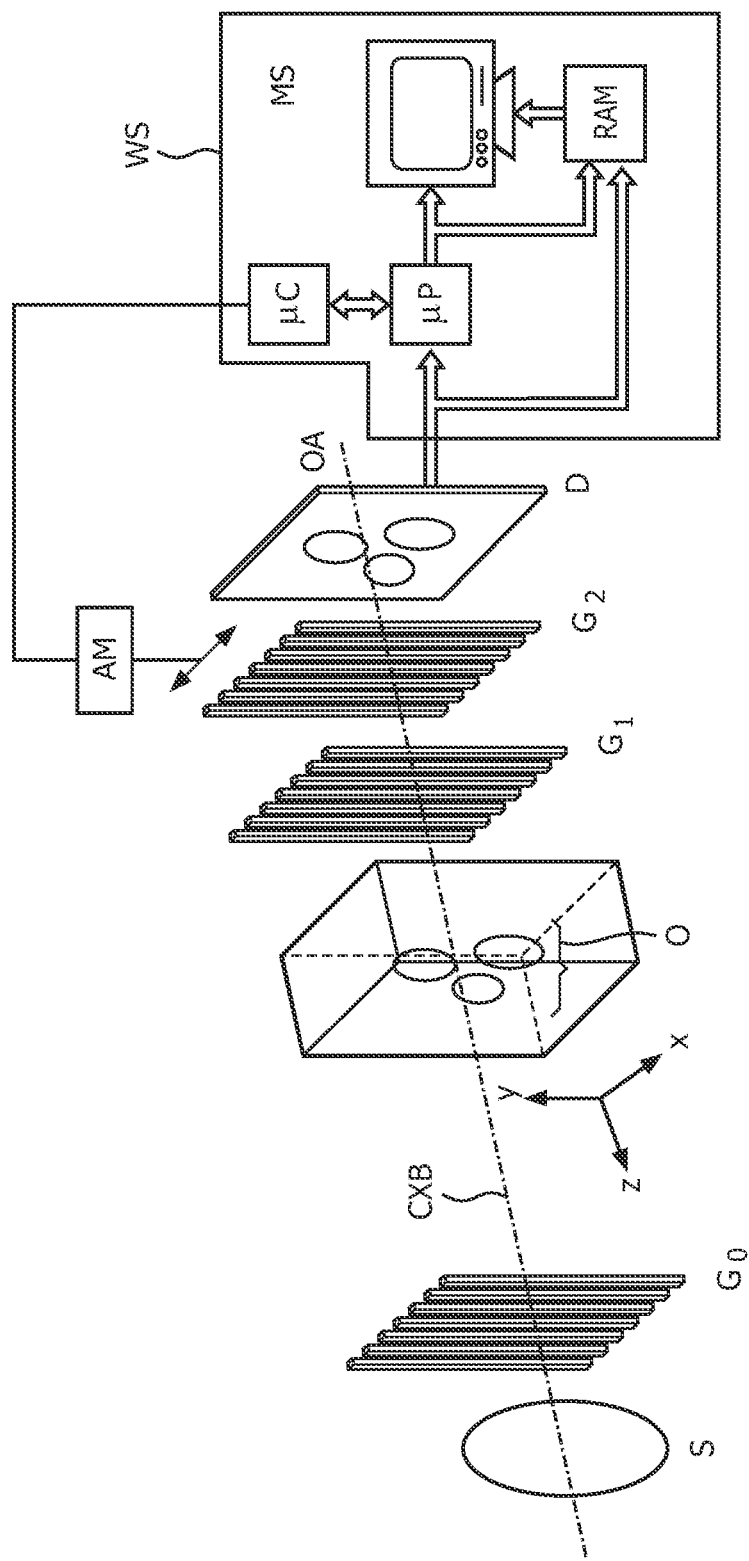
FIG. 1a shows a schematic 3D view of an experimental DPCI setup for a Talbot-Lau type hard-X-ray imaging interferometer as known from the prior art (see F. Pfeiffer et al., Nature Physics 2, 258 (2006))
Figure 1B:
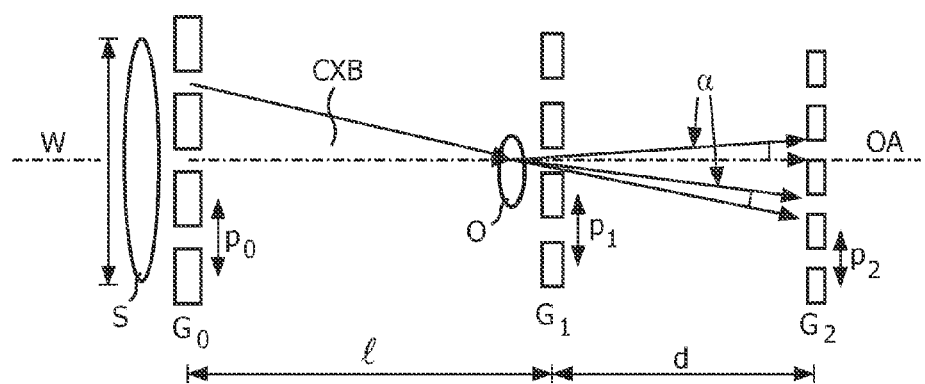
FIG. 1b is a schematic top view of the experimental DPCI setup as depicted in FIG. 1a (ibid.)

The experimental DPCI grating interferometer setup for a Talbot-Lau type hard-X-ray imaging interferometer as known from Pfeiffer and Weitkamp is shown in FIGS. 1a and 1b. Using this kind of interferometer leads to the effect that interfering X-ray beams are not completely separated but merely sheared by a small angle so that they pass through different, closely spaced parts of the sample. The hard-X-ray imaging interferometer of Pfeiffer and Weitkamp comprises an incoherent X-ray source S, a source grating $G_0$ for achieving spatial beam coherence, a diffractive grating $G_1$ (herein also referred to as phase grating) having a plurality of equidistant X-ray absorbing strips extending in parallel in a direction normal to the interferometer's optical axis, which serves as a phase-shifting beam splitter and is placed in downstream direction behind the object, an absorber grating $G_2$ (also referred to as analyzer grating) and an X-ray detector D for detecting the image data of a Moiré interference pattern containing information about the phase shift of the deflected and phase-shifted X-ray beams after passing both the object O and the diffractive grating $G_1$. Moreover, a processing means µP of a workstation WS for recording the image data supplied by said radiation detector in a phase-stepping approach, a non-volatile read-access memory (RAM) for storing these data as well as a monitor screen MS or display for visualizing the recorded image data of the resulting Moiré interference pattern are provided.

Figure 1C:
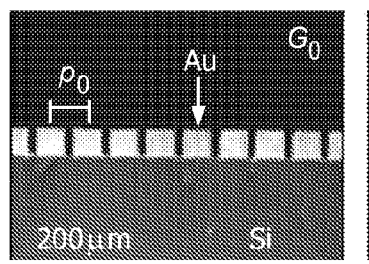
FIG. 1c shows a schematic cross-sectional view of the source grating from the experimental DPCI setup depicted in FIG. 1a with said source grating exhibiting a gold structure on a silicon substrate (ibid.)

Source grating $G_0$, whose structure is depicted in FIG. 1c in a cross-sectional view, creates an array of individually coherent, but mutually incoherent sources. Alternatively to $G_0$, a structured source can be used, where the apertures of $G_0$ are replaced by spatially restricted emission areas of an X-ray source, which is for example represented by a structured anode in an X-ray tube. A phase object O in the beam path causes a slight refraction for each coherent subset of X-rays, which is proportional to the local differential phase gradient of the object. This small angular deviation results in changes of the locally transmitted intensity through the combination of gratings $G_1$ and $G_2$.

Phase grating $G_1$ (see FIG. 1d) acts as a beam splitter and divides an incoming X-ray beam essentially into the two first diffraction orders. Since wavelength λ of the illuminating hard X-rays (which is in the order of below 0.1 nm) is much smaller than the grating pitch (which has a length of about 1 μm), the angle between two diffracted beams is very small. Downstream of phase grating $G_1$, the diffracted beams interfere and form in certain distances known as fractional Talbot distances linear periodic fringe patterns with a periodicity g that equals half the phase grating period $p_1$. It should be noted that the period and the lateral position of these fringes do not depend on the wavelength of the X-rays. Perturbations of the incident wave front, such as those induced by refraction on the object O in the beam, lead to local displacement of the fringes.

However, since phase grating pitch $p_1$ (and thus the spacing of the interference fringes) does not exceed a few micrometers, the imaging detector D placed in the detection plane will generally not have sufficient resolution to resolve the fringes. Therefore, absorber grating $G_2$ (see FIG. 1e), which has the same periodicity and orientation as the fringes, acts as a transmission mask for imaging detector D and transforms local fringe positions into signal intensity variations, and is placed immediately in front of the plane of the imaging detector D. The detected signal profile hence contains quantitative information about the phase gradient $\partial\Phi(x, y)/\partial x$ of the object O. To separate this phase information from other contributions to the signal, such as absorption in the sample, inhomogeneous illumination or imperfections of the gratings, it is known to adapt the phase-stepping approach used in visible-light interferometry to this setup. Thus, two separate images of an object following a process described in more detail in the article "Quantitative X-ray phase imaging with a grating interferometer" (Opt. Express 13 (2005), pp. 6296-6304) by T. Weitkamp, A. Diaz et al. can be derived. The first one represents the amplitude contrast image that would have been received with no interferometer in the beam. It contains mainly absorption contrast and might also contain some in-line phase contrast caused by diffraction on the edges of the sample. The intensity signal of the second image is proportional to the phase shift gradient in the object, which is why it is called the differential phase contrast (DPC) image. The DPC image can be used to obtain the phase profile of the object by a simple one-dimensional integration.

Obviously, the quality of the gratings used in such an interferometer set-up is crucial. To define the grating structures with sufficient accuracy, micro-fabrication techniques are conventionally used. It is essential that the gratings $G_1$ and $G_2$ have the correct ratio of periods. For a plane incoming wave, period $p_2$ of absorber grating $G_2$ should be two times smaller than that of phase grating $G_1$, whereas for a spherical incoming wave, a slight correction needs to be included. Micro lithography techniques need to be used to define the grating line pattern on silicon substrates. The further processing depends on the individual properties required. In particular, phase grating $G_1$ is characterized by low absorbing structures that introduce a phase shift $\Delta\Phi$ of about π radians to the passing X-ray waves, whereas absorber grating $G_2$ is characterized by highly absorbing grating lines. The actual size of the wave front's phase shift $\Delta\Phi$ after transmitting a line structure of phase grating $G_1$ depends on the grating line thickness and on the wavelength λ of the incident X-ray beam. If $G_1$ is irradiated by a plane wave, a periodic interference pattern of intensity is formed in the detector plane that changes as a function of distance d between phase grating $G_1$ and said detector plane. A periodic pattern of linear fringes parallel to the grating lines is for example observed at the first Talbot distance, which is given by $d_1 = p_1^2/8\lambda$. The pitch of these fringes equals half of the periodicity of the phase grating $p_1$. The intensity or amplitude of these fringes depends on $\Delta\Phi$ and shows a maximum modulation for $\Delta\Phi = \pi$ [rad].

In the setup of Pfeiffer and Weitkamp, the structure height of phase grating $G_1$ which is needed to obtain the required phase shift is proportional to the photon energy used. For 17.5 keV, a height of 22 μm is an optimum.

Figure 1D:
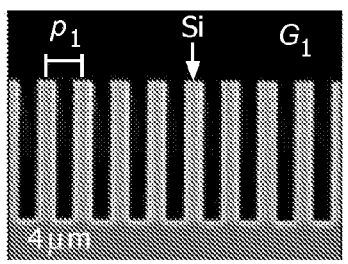
FIG. 1d shows a schematic cross-sectional view of the phase grating from the experimental DPCI setup depicted in FIG. 1a with said phase grating having a 4 µm grating period and exhibiting a 22 µm high silicon (Si) structure (ibid.)

In the setup proposed by these two authors, the period $p_1$ of phase grating $G_1$ is close to 4 μm resulting in very high aspect ratios of the structures. FIG. 1d shows a cross section of such a grating. The structures are made by wet chemical etching in potassium hydroxide solution. As substrates, 250-μm thick silicon wafers with ⟨110⟩ orientation are used. The grating patterns are exposed using a high precision electron beam lithography process. The orientation of the lines is along the ⟨112⟩ direction with a precision of better than 0.1°, which results in an anisotropic etching with vertical side walls. As described in "Wet etched diffractive lenses for hard X-rays" (J. Synchrotron Radiat. 8 (2001), pp. 1054-1055) by C. David, E. Ziegler and B. Nohammer, this process is also used for the fabrication of linear Fresnel zone plates.

Figure 1E:
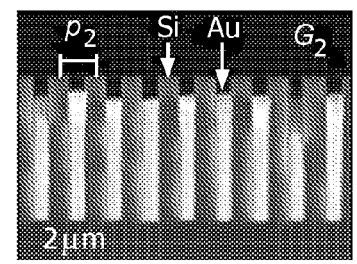
FIG. 1e shows a schematic cross-sectional view of the absorber grating from the experimental DPCI setup depicted in FIG. 1a with said absorber grating having a 2 µm grating period and exhibiting a silicon (Si) structure filled with gold (Au) by electroplating (ibid.)

The fabrication of absorber grating $G_2$ is even more challenging. Firstly, period $p_2$ of the absorber grating has to be two times smaller than that of phase grating $G_1$, i.e. 2 μm, and secondly, no simple etching process exists to pattern highly absorbing materials with high aspect ratios. Structure height again depends on the photon energy. At 17.5 keV, gold is used as an absorbing material. For a high contrast of the DPC signal a structure height of 10 μm is desirable. First, a silicon grating is patterned using the method described above. Then, the gaps of the grating are filled with gold by electro-deposition. Using a shadow evaporation process and selective wet etching, it is possible to let the gold grow from the bottom of the silicon grooves, as any deposition on the side walls or the silicon ridges would result in an incomplete filling of the grooves. FIG. 1e shows a cross section of a gold-filled silicon grating fabricated by the described process which realizes the function of absorber grating $G_2$.

Figure 2:
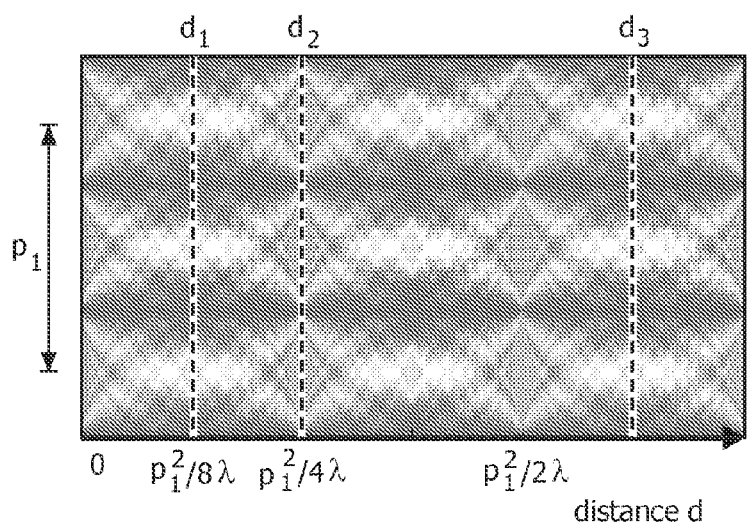
FIG. 2 shows an interference pattern created between the phase grating and the absorber grating of the experimental DPCI setup as depicted in FIG. 1a for demonstrating the "self-imaging" effect of the grid in three characteristic distances—better known as Talbot effect (taken from F. Pfeiffer et al., Phys. Rev. Lett. 94, 164801 (2005))
Figures 3A, 3B, 3C, 3D, 3E:
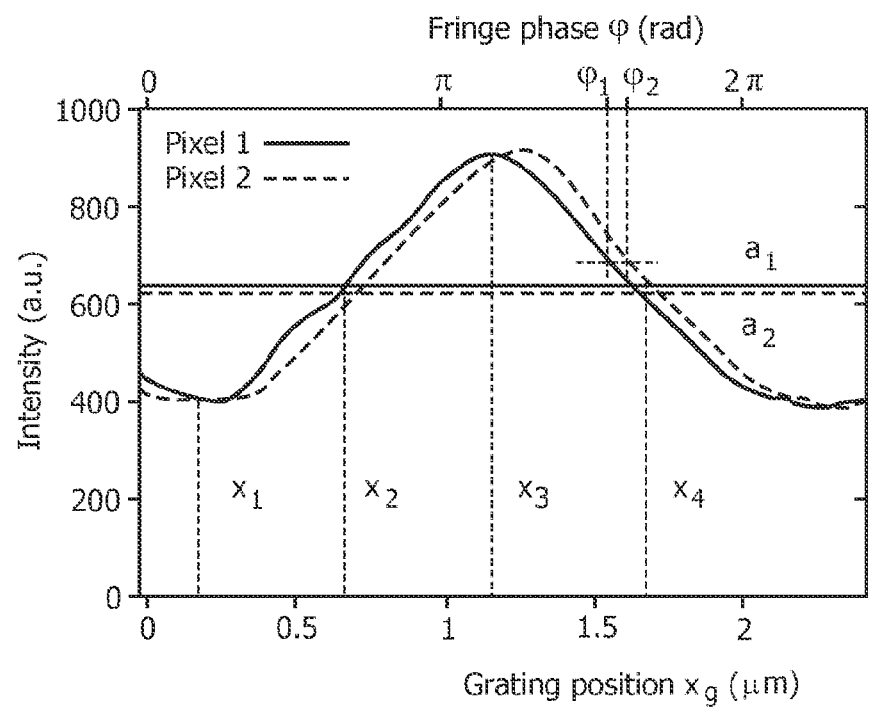
FIGS. 3a-d show four detected X-ray images of an object which are obtained by shifting the absorber grid in a direction x extending parallel to the respective grating planes for illustrating the detection of a "differential phase contrast" (originating from T. Weitkamp et al., Optics Express 13 (16), 6296 (2005))
FIG. 3e shows a shifted interference pattern which is obtained by a grating interferometer due to beam refraction caused by a phase object in the incident X-ray beam on the detector of the experimental DPCI setup of FIG. 1a, which results in changes of the locally transmitted intensity through the analyzer due to a corresponding shift of the diffraction pattern (ibid.), FIGS. 4a+b show two detected X-ray images which exemplarily illustrate the differential phase contrast for two different orientations of the interferometer setup, where the orientations differ by a rotation of 90° around the optical axis, respectively (taken from C. Kottler et al., Optics Express 15 (3), 1175 (2007))

While older (D)PCI methods suffered from the requirement of highly monochromatic and coherent X-ray sources as briefly mentioned above, the method of Pfeiffer and Weitkamp allows the use of standard X-ray sources (i.e. X-ray tubes) equipped with an additional source grating $G_0$ which assures coherence through small openings. The interference pattern (see FIG. 2) which is generated by diffraction of the emitted X-ray beam at phase grating $G_1$ contains the required information about the beam phase shift in the relative positions of the diffraction minima and maxima in the detector plane (which are typically in the order of several micrometers and depend on the phase shift of the wave front incident on the phase grating). FIG. 2 thereby demonstrates the "self-imaging" effect of phase grating $G_1$ (also referred to as Talbot effect) when changing distance d between the planes of the phase grating and the absorber grating to a characteristic value $d_1$, $d_2$ or $d_3$ (with $d_j = j \cdot p_1^2/8\lambda$ denoting the j-th Talbot distance for j=1, 2 or 3) by shifting absorber grating $G_2$ in the direction of the optical axis OA (i.e., in −z-direction) with respect to the z-coordinate of phase grating $G_1$. In currently used DPCI setups, $d_1$ is typically in the order of several centimeters. Since conventional X-ray detectors (which typically have a resolution in the order of about 150 μm) are not able to resolve such fine diffraction structures, the obtained interference pattern is sampled with absorber grating $G_2$, which features a periodic pattern of transmitting and absorbing strips with a periodicity similar to that of the interference pattern. The similar periodicity produces a Moiré pattern behind the absorber grating with a much larger periodicity, which is detectable by common X-ray detectors. To detect the differential phase shift, absorber grating $G_2$ needs to be shifted in x-direction (which means parallel to the particular grating planes) by fractions of the absorber grating period $p_2$, which is typically in the order of about 1 μm—a procedure which is also referred to as "phase stepping". The difference in the wave front phase at two sample positions "1" and "2" can be extracted from the phase shift $\Delta\Phi := \Phi_2 - \Phi_1$ of the Moiré pattern obtained for each position of absorber grating $G_2$, here given at four distinct sampling positions $x_g = x_1, \ldots, x_4$ (see FIGS. 3a-d).

To better understand how the present invention works, the phase integration algorithm as proposed by Kottler et al. shall briefly be explained with reference to the patterns which are depicted in FIGS. 4a-e. Kottler describes that phase retrieval by simple one-dimensional integration along the x-axis may fail to give phase images of satisfactory quality due to occurring artifacts (see FIGS. 4d and 4e) and that there are three main reasons which cause these artifacts. First, if the phase object to be investigated is bigger than the field of view, the boundary conditions and thus the starting wave front profile $\Phi(x=0, y)$ for the integration are unknown. This can exemplarily be seen in FIGS. 4d and 4e where broad shadows are caused by parts of the object (the flower's petal) extending past the boarder of the image. The second cause for artifacts is noise in the phase gradient images. Statistical errors in the determination of the average displacement shift $\langle \Delta x \rangle$ of course depend on counting statistics and the number of $G_2$ phase-steps performed. Statistical uncertainties propagate throughout the integration and thus cause stripes parallel to the direction of integration (see FIG. 4d). Third, phase-wrapping causes similar artifacts as image noise.

The pattern of FIGS. 4d and 4e gives an example of a case where the object fits into the field of view and the phase image is acquired with high statistics, but the integration is not without line artifacts. To overcome these problems, Kottler et al. developed an approach that combines information from two independent directions of integration. The algorithm is similar to the one presented for visible light in "Linear phase imaging using differential interference contrast microscopy" (J. Microsc. 214, pp. 7-12, 2004) by M. R. Arnison et. al. As described in "A two-directional approach for grating based differential phase contrast imaging using hard X-rays" (Optics Express, Vol. 15 (3), 2007, pp. 1175-1181) by C. Kottler et al., the idea is to measure the phase gradient image for both directions x and y, thus $\partial\Phi(x, y)/\partial x$ and $\partial\Phi(x, y)/\partial y$, wherein $\partial\Phi(x, y)/\partial y$ is acquired by rotating the phase object O by 90° around the axis of the central X-ray beam (CXB). When defining a complex phase gradient field $$g(x, y) := \underbrace{\frac{\partial \Phi(x, y)}{\partial x}}_{=:\Phi_x(x,y)} + j \cdot \underbrace{\frac{\partial \Phi(x, y)}{\partial y}}_{=:\Phi_y(x,y)} \quad (2)$$

(with $j := \sqrt{-1}$ being the imaginary unit), its two-dimensional Fourier transform can be written as $$\mathscr{F}[g(x, y)](k, l) = \int_{-\infty}^{+\infty} \int_{-\infty}^{+\infty} g(x, y) \cdot e^{-2\pi j(kx+ly)} dx dy \quad (3)$$
$$= 2\pi j \cdot (k + jl) \cdot \mathscr{F}[\Phi(x, y)](k, l)$$

using the Fourier derivative theorem, where (k, l) represent the spatial frequency coordinates corresponding to (x, y). Therefore, wave front profile $\Phi(x, y)$ can be obtained by submitting equation (2) to an inverse Fourier transform, which yields:

$$\Phi(x, y) = \mathscr{F}^{-1}\left[\frac{\mathscr{F}[\Phi_x(x, y) + j \cdot \Phi_y(x, y)](k, l)}{2\pi j \cdot (k + jl)}\right](x, y). \quad (4)$$

In FIGS. 5a-c, it is exemplarily illustrated how the proposed method according to the present invention works. Essentially, the information of the acquired X-ray image which is obtained in the detector plane after the transmitted X-ray beam passes absorber grating $G_2$ (herein also referred to as "absorption image") is used to detect strong phase gradients in the absorption image.

In a first step, as absorption and phase shift are related to each other (both are directly dependent on the electron density of object O), pixels of strong phase gradient can be marked as "bad" and correspondingly considered to potentially induce phase errors of $2\pi$ radians. In a second step, the integrated phase gradient image is analyzed for characteristic line artifacts starting from pixels which are marked as "bad". If the analysis indicates that a phase offset of $2\pi$ to neighbored lines or an integer multiple thereof exists after "passing" a pixel which has been marked as bad, a correction phase offset of $2\pi$ radians or an integer multiple thereof is introduced at the position of the bad pixel, and the integral phase gradient image is recalculated.

FIG. 5a shows a diagram which illustrates the above-described situation of phase wrapping induced by random pixel noise. A special situation occurs if an image area is surrounded by "bad pixels" (e.g. due to an object boundary). FIG. 5b shows such a situation of phase wrapping inside and outside an image area which is surrounded by bad pixels. In this case, it could be useful to estimate the number of $2\pi$ phase offset errors inside of that area relative to the outside area by separately averaging the phase offsets in these two areas and applying a whole-area offset given by the sum over a number of $2\pi$ phase offsets which fit best to the difference between the two determined average values. In a last step, the phase shifts of bad pixels are interpolated from that of good pixels in the neighborhood of these bad pixels. A diagram which shows the depicted image area of FIG. 5b after correction of the phase wrapping is shown in FIG. 5c.

To be more precisely, the claimed method according to the present application proposes to perform the following steps:
1. Estimating a "starting" phase offset at the left image border (which might be trivial if phase object O does not extend over the left image border). Otherwise, for the left image border, a phase offset is estimated line-by-line from the absorption image.
2. Analyzing the absorption image for strong gradients and/or noisy pixels and marking them as "bad".
3. Calculating a line integral in x-direction over the local phase gradient (i.e., restoring the absolute phase).

4. Performing an image segmentation for areas of good pixels.
5. For each area, choosing a reference line and estimating an absolute phase from the absorption image (e.g., choosing the longest "healthy looking" line segment) and checking if lines in the phase image differ to neighbored lines by a phase offset near $2\pi$ within good pixels. If yes, the next left-sided bad pixel in the differential phase image is searched and corrected modulo $2\pi$ (which means that the obtained phase image must be recalculated thereafter). After that, step 5 is repeated until no more systematic line artifacts exhibiting a phase difference of $2\pi$ radians or an integer multiple thereof are found within the image area.
6. Interpolating bad pixels, e.g. by estimating the phase offset directly from the local phase gradient of the absorption image.

For the "bad" pixels, an alternative way of interpolation could be performed within the phase gradient image in the following way: Within the good-pixel area in the vicinity of the pixel to be interpolated, a correlation plot may be performed for the measured phase difference versus the measured difference in the absorption image, eventually by using a statistical smoothing function.

Under the assumption that noise is not a limiting factor, one should see an almost linear dependency between these two quantities. For a bad pixel, it is assumed that it deviates from this linear correlation plot by a phase offset of $\Phi_k = k \cdot 2\pi$ (with k being an integer). The phase of each "bad" pixel may then be corrected by a value of $\Phi_k$ where k is chosen such that the pixel error between the corrected phase and the determined relationship between absorption gradient and phase shift becomes minimal.

APPLICATIONS OF THE PRESENT INVENTION

The main applications of the invention are found in all modalities related to differential phase contrast imaging (DPCI), i.e. in stationary transmission geometries (i.e. mammography, fluoroscopy etc.), but also in computed tomography (CT) or related rotational X-ray imaging technologies.

While the present invention has been illustrated and described in detail in the drawings and in the foregoing description, such illustration and description are to be considered illustrative or exemplary and not restrictive, which means that the invention is not limited to the disclosed embodiments. Other variations to the disclosed embodiments can be understood and effected by those skilled in the art in practicing the claimed invention, from a study of the drawings, the disclosure and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures can not be used to advantage. It should further be noted that any reference signs in the claims should not be construed as limiting the scope of the invention.

The invention claimed is:

1. An apparatus, serving as an interferometer setup and having an optical axis, said apparatus for imaging an object by means of electromagnetic waves or matter waves, wherein the object causes an altered phase information of the electromagnetic waves or matter waves according to a local refraction index, the apparatus comprising;
   a radiation source for emitting the electromagnetic waves or matter waves for transmission through said object;
   a radiation detector for detecting these electromagnetic waves or matter waves; and
   a pixel-correcting processor configured for gaining information representative of the object's local phase gradient ($\partial\Phi(x, y)/\partial x$) in at least one transverse direction perpendicular to the interferometer setup's optical axis,
   wherein said processor is configured for determining the pixel positions of noisy pixels and/or determining at which pixel positions of a detected phase gradient image the local phase gradient exceeds a predefined threshold value and marking these pixels as "bad", performing a line integration over the local phase gradient, thus yielding an integrated phase gradient image, analyzing the integrated phase gradient image for characteristic line artifacts occurring behind pixels of strong phase gradient which have been marked as "bad" and introducing a correction phase offset of $2\pi$ radians or an integer multiple thereof at the position of each "bad" pixel if analysis shows that a measured $2\pi$ phase offset error or an integer multiple thereof between immediately adjacent line artifacts which is induced by said line integration persists after passing a pixel that has been marked as "bad" so as to compensate said $2\pi$ phase offset error or an integer multiple thereof.

2. The apparatus according to claim 1, in which said electromagnetic waves are given by X-ray radiation.

3. The apparatus according to claim 2, comprising, as said setup, a DPCI-based grating interferometer setup of the Talbot-Lau type for differential phase contrast imaging, said DPCI-based interferometer setup including:
   at least one source grating for achieving spatial beam coherence, realized as an arrayed aperture mask with periodically modulated transmission and placed in downstream direction immediately behind the radiation source;
   at least one diffractive grating with a periodic structure, which serves as a phase-shifting beam splitter generating self-images according to the Talbot effect;
   at least one analyzer grating placed behind the at least one diffractive grating and in front of the radiation detector, wherein said radiation detector comprises a wave absorber with a periodical structured attenuation strength based on a self-image of the at least one diffractive grating; and
   a volume which is large enough to place the object to be imaged anywhere between the at least one source grating and the at least one analyzer grating.

4. The apparatus according to claim 3, comprising at least one grating-shifting actuator configured for shifting at least one of the gratings in a direction perpendicular to the optical axis and parallel to at least one direction which contains a periodicity of the self-image of when carrying out a phase-stepping approach, and further comprising a controller configured for controlling said actuator means in such a way that at least one of said gratings is shifted by predefined fractions of the periodicity of the diffractive grating's self-image in accordance with said phase-stepping approach.

5. The apparatus according to claim 4, where the at least one source grating is either replaced by a wave source with a spatially modulated intensity distribution corresponding to the apertures of the replaced at least one source grating or by an array of at least one point source, wherein "point" represents an emission area small enough to fulfill the requirements of spatial coherence.

6. The apparatus according to claim 5, wherein the at least one source grating and the at least one analyzer grating are both realized as a periodic structure comprising a number of stripes oriented in parallel to a first direction perpendicular to the optical axis for creating an interference pattern which basically obtains a periodical modulation along a second direction perpendicular to the first direction and perpendicular to the optical axis.

7. The apparatus according to claim 5, wherein the at least one source grating and the at least one analyzer grating are both realized as a periodic structure given by a two-dimensional array or lattice structure exhibiting a periodicity in at least two directions perpendicular to the optical axis for creating an interference pattern which basically obtains a periodical modulation along at least two directions perpendicular to the optical axis.

8. The apparatus according to claim 2, in which said local phase gradient ($\partial\Phi(x, y)/\partial x$) is measured by use of coded apertures, characterized by at least two structured wave absorbing masks arranged behind the radiation source, wherein a first mask of these at least two structured wave absorbing masks provides a plurality of wave beams having cross-sectional areas perpendicular to the beam direction which do not overlap each other, said wave beams optionally transmitting image information of the object to be imaged, and wherein a second mask of the at least two structured wave absorbing masks partially covers each of the cross-sectional areas of said wave beams before being detected by the radiation detector, wherein the cross-sectional area of each wave beam covered by said second mask and thus the signal detected by the radiation detector depends on the deflection of said wave beam proportional to the local phase gradient ($\partial\Phi(x, y)/\partial x$).

9. A method for, via an interferometer setup for imaging an object by means of electromagnetic waves or matter waves, reducing the influence of induced phase errors on image quality, said setup having an optical axis, wherein the object causes an altered phase information of the electromagnetic waves or matter waves according to a local refraction index, said setup comprising a radiation source for emitting electromagnetic waves or matter waves for transmission through said object, a radiation detector for detecting these electromagnetic waves or matter waves and a pixel-correcting processor for gaining information representative of the object's local phase gradient ($\partial\Phi(x, y)/\partial x$) in at least one transverse direction perpendicular to the interferometer setup's optical axis,
wherein said method comprises the steps of:
determining the pixel positions of noisy pixels and/or determining at which pixel positions of a detected phase gradient image the local phase gradient exceeds a predefined threshold value and marking all these pixels as "bad";
performing a line integration over the local phase gradient, thus yielding an integrated phase gradient image;
analyzing the integrated phase gradient image for characteristic line artifacts occurring behind pixels of strong phase gradient which have been marked as "bad"; and
introducing a correction phase offset of $2\pi$ radians or an integer multiple thereof at the position of each "bad" pixel if analysis shows that a measured $2\pi$ phase offset error or an integer multiple thereof between immediately adjacent line artifacts which is induced by said line integration persists after passing a pixel that has been marked as "bad" so as to compensate this $2\pi$ phase offset error or an integer multiple thereof.

10. The method according to claim 9, used for reducing the influence of induced phase errors on the image quality of a DPCI-based grating interferometer setup of the Talbot-Lau type for hard X-ray phase contrast imaging.

11. The method according to claim 10, which, in case of detecting an image area within the interference pattern of the detected X-ray image that is completely surrounded by "bad" pixels, comprises the step of estimating the number of $2\pi$ phase offset errors within this image area relative to the number of $2\pi$ phase offset errors outside this image area by calculating an averaged number of $2\pi$ phase offset errors both over the inside area and over the outside area and by applying a whole-area phase correction offset given by the sum over a number of $2\pi$ phase offsets which fits best to the difference of the two calculated average values.

12. The method according to claim 11, comprising the step of interpolating the phase offsets of "bad" pixels from those of "good" pixels in the neighborhood of said "bad" pixels.

13. The method according to claim 12, wherein information of an available absorption image is used for a better estimation of a correction offset for "bad" pixels.

14. Use of a method according to claim 9 in a medical X-ray radiography, 3D rotational angiography or computed tomography application scenario for enhancing the image quality of acquired X-ray images.

15. A non-transitory computer readable medium embodying a program for, via an interferometer setup for imaging an object by means of electromagnetic waves or matter waves, reducing the influence of induced phase errors on the image quality of an apparatus serving as said setup, said setup having an optical axis, wherein the object causes an altered phase information of the electromagnetic waves or matter waves according to a local refraction index, the apparatus comprising a radiation source for emitting electromagnetic waves or matter waves for transmission through said object, a radiation detector for detecting these electromagnetic waves or matter waves and a pixel-correcting processor for gaining information representative of the object's local phase gradient ($\partial\Phi(x, y)/\partial x$) in at least one transverse direction perpendicular to the interferometer setup's optical axis, said program having instructions executable by a processor for carrying out a plurality of acts, among said plurality there being the acts of:
determining the pixel positions of noisy pixels and/or determining at which pixel positions of a detected phase gradient image the local phase gradient exceeds a predefined threshold value and marking all these pixels as "bad";
performing a line integration over the local phase gradient, thus yielding an integrated phase gradient image;
analyzing the integrated phase gradient image for characteristic line artifacts occurring behind pixels of strong phase gradient which have been marked as "bad"; and
introducing a correction phase offset of $2\pi$ radians or an integer multiple thereof at the position of each "bad" pixel if analysis shows that a measured $2\pi$ phase offset error or an integer multiple thereof between immediately adjacent line artifacts Which is induced by said line integration persists after passing a pixel that has been marked as "bad" so as to compensate this $2\pi$ phase offset error or an integer multiple thereof.

16. The computer readable medium of claim 15, said determining the pixel positions of noisy pixels, and/or said determining at which pixel positions of a detected phase gradient image the local phase gradient exceeds a predefined threshold value, entailing employing an absorption image to detect phase wrappings.

17. The computer readable medium of claim 16, an absorber grating being disposed behind a diffractive grating and in front of said radiation detector, said absorption image comprising image information obtained in the detector after radiation conveying said image information has passed through said absorber grating.

18. The apparatus of claim 1, configured for, in said determining the pixel positions of noisy pixels and/or determining at which pixel positions of a detected phase gradient image the local phase gradient exceeds a predefined threshold value, employing an absorption image to detect phase wrappings.

19. The apparatus of claim 18, an absorber grating being disposed behind a diffractive grating and in front of said radiation detector, said absorption image comprising image information obtained in the detector after radiation conveying said image information has passed through said absorber grating.

20. The method of claim 9, said determining the pixel positions of noisy pixels, and/or said determining at which pixel positions of a detected phase gradient image the local phase gradient exceeds a predefined threshold value, entailing employing an absorption image to detect phase wrappings.

\* \* \* \* \*